(12) United States Patent
Liang et al.

(10) Patent No.: US 6,387,662 B1
(45) Date of Patent: May 14, 2002

(54) SYNTHESIS AND PURIFICATION OF HEPATITIS C VIRUS-LIKE PARTICLES

(75) Inventors: T. Jake Liang, Potomac; Thomas F. Baumert, Bethesda, both of MD (US)

(73) Assignee: The United States of America as represented by the Department of Health & Human Services, Washington, DC (US)

( * ) Notice: Subject to any disclaimer, the term of this patent is extended or adjusted under 35 U.S.C. 154(b) by 0 days.

(21) Appl. No.: 09/296,441

(22) Filed: Apr. 21, 1999

Related U.S. Application Data

(63) Continuation of application No. PCT/US97/05096, filed on Mar. 25, 1997.
(60) Provisional application No. 60/030,238, filed on Nov. 8, 1996.

(51) Int. Cl.$^7$ ............................................... C12N 15/09
(52) U.S. Cl. ........................ 435/69.3; 435/5; 435/236; 435/239; 424/196.11; 424/228.1; 530/350
(58) Field of Search ..................... 530/350; 424/196.11, 424/228.1; 435/236, 69.3, 5, 239

(56) References Cited

U.S. PATENT DOCUMENTS

| | | |
|---|---|---|
| 3,645,852 A | 2/1972 | Axen et al. |
| 4,861,711 A | 8/1989 | Friesen et al. |
| 4,956,302 A | 9/1990 | Gordon et al. |
| 5,096,837 A | 3/1992 | Fan et al. |
| 5,372,928 A | 12/1994 | Miyamura et al. |
| 5,521,102 A | 5/1996 | Boehringer et al. |
| 5,670,153 A | 9/1997 | Weiner et al. |
| 5,698,390 A | 12/1997 | Houghton et al. |
| 5,712,088 A | 1/1998 | Houghton et al. |
| 5,714,596 A | 2/1998 | Houghton et al. |
| 5,756,312 A | 5/1998 | Weiner et al. |
| 5,766,845 A | 6/1998 | Weiner et al. |
| 5,942,234 A * | 8/1999 | Ralston et al. ............ 424/228.1 |

FOREIGN PATENT DOCUMENTS

| | | |
|---|---|---|
| EP | 0 323 605 | 7/1989 |
| EP | 0 577 894 | 1/1994 |
| WO | WO 91/02820 | 3/1991 |
| WO | WO 92/08734 | 5/1992 |
| WO | WO 95/33053 | 12/1995 |
| WO | WO 96/04301 | 2/1996 |

OTHER PUBLICATIONS

Heinz et al., Recombinant and virion–derived soluble and particulate immunogens for vaccination against tick–borne encephalitis. Vaccine 13(17):1636–1642, 1995.*
Heile et al., Evaluation of Hepatitis C Virus Glycoprotein E2 for Vaccine Design: an Endoplasmic Reticulum–Retained Recombinant Protein Is Superior to Secreted Recombinant Protein and DNA–Based Vaccine Candidates. Journal of Virology 74(15):6885–6892, 2000.*
Mast et al., Strategies to prevent and control hepatitis B and C virus infections: a global perspective. Vaccine 17:1730–1733, 1999.*
Baumert, T.F., et al., Hepatitis C Virus Structural Proteins Assemble into Viruslike Particles in Insect Cells, Journal of Virology, May, 1998, pp. 3827–3836.
Alter et al., *New England Journal of Medicine*, 321: 1494–1500, 1989, "Detection of Antibody to Hepatitis C Virus in Prospectively Followed Transfusion Recipients with Acute and Chronic Non–A, Non–B Hepatitis."
Baumert et al., *Hepatology*, vol. 24, No. 4, Part 2, p. 251, Abstract No. 500, 1996, "Synthesis of Hepatitis C Virus Like Particles in Insect Cells."
Berman, *Science*, 222: 524–527, 1983 *Proc. Natl. Acad. Sci. USA*, 81: 659–663, 1984, "Detection of Antibodies to Herpes Simplex Virus with a Continuous Cell Line Expressing Cloned Clycoprotein D."
Bielefeldt & Block, *Arch. Virol.*, 71: 57–74, 1981, "Electron Microscopic Studies of Bovine Viral Diarrhea Virus in Tissues of Diseased Calves and in Cell Cultures."
Brinster et al., *Nature*, 296: 39–42, 1982, "Regulation of Metallothionein–thymidine kinase fusion plasmids injected into mouse eggs."
Choo et al., *Science*, 244: 359–362, 1989, "Isolation of a cDNA Clone Derived from a Blood–Borne Non–A, Non–B Viral Hepatitis Genome."
Dubuisson et al., *J. Virol.* 68: 6147–6160, 1994, "Formation and Intracellular Localization of Hepatitis C Virus Envelope Glycoprotein Complexes Expressed by Recombinant Vaccinia and Sindbis Viruses."
Feinstone et al., *Infect. Immun.*, 41: 816–821, 1983, "Inactivation of Hepatitis B Virus and Non–A, Non–B Hepatitis by Chloroform."
Francki et al., eds., Classification and Nomenclature of Viruses, *Arch. Virol.*, Supp. 2: 223–233, 1991.
GenBank data base accession No. D90208, Definition: Hepatitis C virus genomic RNA.
GenBank data base accession No. D00757, Definition: Hepatitis C virus genomic RNA.
Gheysen et al., *Cell*, 59: 103–112, 1989, "Assembly and release of HIV–1 Precursor Pr55$^{gag}$ Virus–like Particles from Recombinant Baculovirus–Infected Insect Cells."
Grakoui et al., *J. Virol.*, 67: 1385–1395, 1993, "Expression and Identification of Hepatitis C Virus Polyprotein Cleavage Products."

(List continued on next page.)

Primary Examiner—Donna C. Wortman
(74) Attorney, Agent, or Firm—Knobbe, Martens, Olson & Bear LLP

(57) ABSTRACT

Production of enveloped RNA virus-like particles intracellularly in vitro in insect cells using a recombinant baculovirus vector containing a cDNA coding for viral structural proteins is disclosed. In vitro production and purification of hepatitis C virus (HCV)-like particles containing HCV core protein, E1 protein and E2 protein is disclosed. Production of antibodies in vivo to the purified HCV-like particles is disclosed.

11 Claims, 1 Drawing Sheet

OTHER PUBLICATIONS

Grakoui et al., *Proc. Natl. Acad. Sci. USA*, 90: 10583–10587, 1993, "A second hepatitis C virus–encoded proteinase."

Gray & Nettleton, *J. Gen. Virol.*, 68: 2339–2346, 1987, "The Ultrastructure of Cell Cultures Infected with Border Disease and Bovine Virus Diarrhoea Viruses."

He et al., *J. Infect. Dis.*, 156: 636–640, 1987, "Determining the Size of Non–A, Non–B Hepatitis Virus by Filtration."

Hijikata et al., *Proc. Natl. Acad. Sci. USA*, 88: 5547–5551, 1991, "Gene mapping of the putative structural region of the hepatitis C virus genome by in vitro processing analysis."

Hijikata et al., *J. Virol.*, 67: 1953–1958, 1993, "Equilibrium Centrifugation Studies of Hepatitis C Virus: Evidence for Circulating Immune Complexes."

Hoofnagle & DiBiscecile, *New England Journal of Medicine*, 336: 347–356, 1997, "The Treatment of Chronic Viral Hepatitis."

Hsu et al., *Hepatol.*, 17(5): 763–771, 1993, "Characterization of Hepatitis C Virus Structural Proteins with a Recombinant Baculovirus Expression System."

Judd, R., Methods in Enzymology: Guide to Protein Purification, 182: 613–626, 1990, "Peptide Mapping."

Kaito et al., *J. Gen. Virol.*, 75: 1755–1760, 1994, "Hepatitis C virus particle detected by immunoelectron microscopic study."

Kato et al., *Proc. Natl. Acad. Sci. USA*, 87: 9524–9528, 1990, "Molecular cloning of the human hepatitis C virus genome from Japanese patients with non–A, non–B hepatitis."

Kirnbauer et al., *Pro. Natl. Acad. Sci. USA*, 89: 12180–12184, 1992, "Papillomavirus L1 major capsid protein self–assembles into virus–like particles that are highly immunogenic."

Kuo et al., *Science*, 244: 362–364, 1989, "An Assay for Circulating Antibodies to a Major Etiologic Virus of Human Non–A, Non–B Hepatitls."

Lanford et al., *Virol.*, 197: 225–235, 1993, "Analysis of Hepatitis C Virus Capsid, E1, and E2/NS1 Proteins Expressed in Insect Cells."

Langer, *Science*, 249: 1527–1533, 1990, "New Methods of Drug Delivery."

Lemon & Thomas, *New England Journal of Medicine*, 336: 177–203, 1997, "Vaccines to Prevent Viral Hepatitis."

Lesiewski et al., *J. Med. Virol.*, 45: 415–422, 1995, "Antibody to Hepatitis C Virus Second Envelope (HCV–E2) Glycoprotein: A New Marker of HCV Infection Closely Associated with Viremia."

Lin et al., *J. Virol.*, 68(8): 5063–5073, 1994, "Processing in the Hepatitis C Virus E2–NS2 Region: Identification of p7 and Two Distinct E2–Specific Products with Different C Termini."

Lo et al., *J. Virol.*, 70(6): 5177–5182, 1996 (may be No. 8) "Interaction between Hepatitis C Virus Core Protein and E1 Envelope Protein."

Luckow & Summers, *Virol.*, 167: 56, 1988, "Signals Important for High–Level Expressionof Foreign Genes in *Autographa califomica* Nuclear Polyhedrosis Virus Expression Vectors."

Luckow et al., *J. Virol.*, 67: 4566, 1993, "Efficient Generation of Infectious Recombinant Baculoviruses by Site–Specific Transposon–Mediated Insertion of Foreign Genes into a Baculovirus Genome Propagated in *Escherichia coli*."

Matsuura & Miyamura, *Seminars in Virol.*, 4: 297–304, 1993, "The molecular biology of hepatitis C virus."

Matsuura et al., *J. Virol.*, 66: 1425–1431, 1992, "Expression of Processed Envelope Protein of Hepatitis C Virus in Mammalian and Insect Cells."

Matsuura et al., *Virol.*, 205: 141–150, 1994, "Processing of E1 and E2 Glycoproteins of Hepatitis C Virus Expressed in Mammalian and Insect Cells."

Miyamoto et al., *J. Gen. Virol.*, 73: 715–718, 1992, "Extraordinarily low density of hepatitis C virus estimated by sucrose density gradient centrifugation and the polymerase chain reaction."

Miyamura & Matsuura, *Trends Microbiol.*, 1(6): 229–231, 1993, "Structural proteins of hepatitis C virus."

Mizuno et al., *Gastroenterol.*, 109(6): 1933–1940, 1995, "Virion–like Structures in HeLa G Cells Transfected With the Full–Length Sequence of the Hepatitis C Virus Genome."

Peterson et al., *Nature*, 276: 269–270, 1978, "Activation of latent Epstein–Barr virus by antibody to human IgM."

Reynolds et al., *EMBO J.*, 14: 6010–6020, 1995, "Unique features of internal initiation of hepatitis C virus RNA translation."

Rice, Fields Virology, Lippincott–Raven Publishers, pp. 931–959, 1996, "Flaviviridae: the viruses and their replication."

Shimizu et al., *Hepatol.*, 23(2): 205–209, 1996, "Hepatitis C Virus: Detection of Intracellular Virus Particles by Electron Microscopy."

Shindo et al., *Proc. Natl. Acad. Sci. USA*, 91: 8719–8723, 1994, "The physical state of the negative strand of hepatitis C virus RNA in serum of patients with chronic hepatitis C."

Thomsen et al., *Journal of General Virology*, vol. 73, Part 7, pp. 1819–1824, 1992, "Expression of Feline Leukaemia Virus gp85 and gag Proteins and Assembly Into Virus–Like particles Using the Baculovirus Expression Vector System."

Thomsen et al., *Proc. Natl. Acad. Sci. USA*, 81: 659–663, 1984, "Promoter–regulatory region of the major immediate early gene of human cytomegalovirus."

Thomssen et al., *Med. Microbiol. Immunol.*, 181: 292–300, 1992, "Association of hepatitis C virus in human sera with β–lipoprotein."

Tong et al., *New England Journal of Medicine*, 332: 1463–1466, 1995, "Clinical Outcomes After Transfusion –Associated Hepatitis C."

Zeng et al., *J. Virol.*, 70: 2736–2742, 1996, "Characterization and Replicase Activity of Double–Layered and Single –Layered Rotavirus–Like Particles Expressed from Baculovirus Recombinants."

\* cited by examiner

SYNTHESIS AND PURIFICATION OF HEPATITIS C VIRUS-LIKE PARTICLES

RELATED APPLICATIONS

This application is a continuation of and claims the benefit of priority of International Application No. PCT/US97/05096 designating the U.S. having International filing date of Mar. 25, 1997, in English, abandoned, claims the benefit of priority of U.S. patent application No. 60/030,238, filed Nov. 8, 1996, in English.

BACKGROUND OF THE INVENTION

Hepatitis C virus (HCV) is a major causative agent of post-transfusion and community-acquired non-A, non-B hepatitis world-wide (Kuo, G. et al., Science 244:362–364, 1989; Choo O. L. et al., Science 244:359–362, 1989; Alter H. J. et al., N. Engl. J. Med. 321:1494–1500, 1989; Kato N. et al., Proc. Natl. Acad. Sci. USA 87: 9524–9528, 1990). The majority of HCV infected individuals develop chronic hepatitis which progresses eventually to liver cirrhosis and hepatocellular carcinoma (Tong M. J. et al., N. Engl. J. Med. 332:1463–1466, 1995). Currently, no effective vaccine to prevent HCV infection or treatment for chronic HCV infection exists (Lemon, S. M. & Thomas, D. L., New Engl. J. Med. 336:177–203, 1997; Hoofuagle, J. & DiBisceclie, New Engl. J. Med. 336:347–356, 1997). Development of an effective vaccine and/or treatment has been hampered by the inability to propagate HCV efficiently in cultured cells and the lack of a small animal model.

HCV is a member of the flavivirus family (; Francki R. I. B. et al., Arch. Virol., Suppl. 2.223–233, 1991). The HCV virion contains a positive-strand RNA genome of 9.5 kilobases (kb) including a highly conserved 5' noncoding region followed by a long open reading frame of 9030 to 9099 nucleotides (nt) that is translated into a single polyprotein of about 3,010 to 3,030 amino acids (Matsuura Y. & Miyamura T., Seminars in Virol. 4:297–304, 1993; Hijikata M. et al., Proc. Natl. Acad. Sci. USA 88:5547–5551, 1991). Initiation of translation occurs by a mechanism of internal ribosomal entry requiring the 5' untranslated region (UTR) and a short stretch of HCV coding sequences (Reynolds J. E. et al, EMBO J. 14:6010–6020, 1995). Processing of the polyprotein occurs by a combination of host and viral proteases to produce at least ten putative viral structural and nonstructural (NS) proteins. The HCV structural proteins comprise the nucleocapsid or core protein (C) and the two putative virion envelope glycoproteins E1 and E2 (Miyamura T. & Matsuura Y., Trends Microbiol. 1(6):229–231, 1993). The cleavage of structural proteins from the polyprotein is catalyzed by a host signal peptidase (Hijikata M. et al., Proc. Natl. Acad. Sci. USA 88:5547–5551, 1991; Lin C. et al., J. Virol. 68(8):5063–5073, 1994), whereas polyprotein cleavage in the nonstructural region requires the presence of HCV-encoded proteinases encoded by the nonstructural region (Grakoui A. et al., Proc. Natl. Acad. Sci. USA 90:10583–10587, 1993).

Although the viral genomic organization has been characterized in detail, morphologic analysis of hepatitis C virus has been hampered by low levels of HCV particles in infected patients and the inability to propagate efficiently the virus in cultured cells. The levels of the viral particles present in infected patient plasma and/or liver tissues are very low, making it difficult to visualize the virus. By analogy to other members of the Flaviviridae, the HCV genomic organization suggests a virus consisting of a nucleocapsid comprising a viral genome and core protein coated by a lipid envelope containing the envelope glycoproteins E1 and E2. Studies of HCV infection in chimpanzees, a reliable animal model for hepatitis C, have provided evidence that HCV is inactivated by chloroform, indicating that it contains essential lipids and therefore is probably enveloped (Feinstone, S. M. et al., Infect. Immun. 41:816–821, 1983). Filtration studies have estimated the virion particle size to be about 30–60 nm in diameter (He et al., J. Infect. Dis. 156:636–640, 1987).

Recombinant HCV proteins have been produced using various expression systems, but no virus-like particles have been generated in these systems (Grakoui A. et al., J. Virol. 67:1385–1395, 1993; Hijikata, M. et al., Proc. Natl. Acad. Sci. USA 88:5547–5551, 1991; LauFord, B. et al., Virol. 197:225–235, 1993; Miyamura, T. & Matsuura, Y., Trends Microbiol. 1:229–231, 1993). Production of recombinant HCV proteins suggests that some of the HCV proteins specifically interact. For example, previous results suggest that the HCV core protein interacts with the E1 envelope protein but not with the E2 envelope protein (Lo S.-Y. et al., J. Virol. 70(6): 5177–5182, 1996). Recombinant HCV polypeptides produced in vitro have been disclosed in PCT application WO 9604301, PCT application WO 9533053, PCT application WO 9102820 and U.S. Pat. No. 5,372,928.

Virus-like particles have been synthesized for viruses of various families other than Flaviviridae or Pestiviridae using a baculovirus-insect cell expression system (Gheysen D. et al., Cell 59:103–112, 1989; Kirnbauer R. et al., Proc. Natl. Acad. Sci. USA 89:12180–12184; 1992; Zeng C. O.-Y. et al., J. Virol. 70:2736–2742, 1996). The baculovirus-insect cell expression of viral proteins is advantageous because the eukaryotic insect cells can carry out a number of co- or post-translational modifications such as fatty acid acetylation and glycosylation, similar to mammalian cells (Luckow, V. A. & Summers, M. D., Virol. 167:56, 1988). Moreover, the baculovirus expression system allows higher levels of heterologous protein synthesis than generally is possible in many mammalian cell expression systems (Luckow, V. A. & Summers, M. D., Viral. 167:56, 1988).

The present invention differs from the prior art because it utilizes a recombinant construct that contains nucleic acid that includes part of the 5' UTR, coding sequences for HCV structural proteins including p7, and produces virus-like particles when the construct is expressed in insect cells. These virus-like particles of an enveloped RNA virus are generated without other components required for viral replication and are assembled intracellularly in vitro. These virus-like particles are effective immunogens for generating HCV-specific antibodies and thus are important for development of an effective HCV vaccine.

SUMMARY OF THE INVENTION

According to one aspect of the invention, there is provided a method of producing virus-like particles in vitro comprising the steps of providing a vector comprising an expression system capable of producing proteins in insect cells, cloning a cDNA that codes for structural proteins of an enveloped RNA virus into the vector such that the cDNA is capable of being expressed in transfected or infected insect cells, transfecting or infecting insect cells with the vector containing the cloned cDNA that codes for the structural proteins of an enveloped RNA virus, maintaining the transfected or infected insect cells in culture for sufficient time to allow expression of the cDNA to produce the structural proteins of an enveloped RNA virus, and allowing the structural proteins to form intracellular virus-like particles.

In one embodiment, the method further comprises the step of purifying the intracellular virus-like particles from the cultured cells. In a preferred embodiment, the purifying step comprises lysing the cells to produce a lysate and subjecting the lysate to gradient centrifugation. In another embodiment, the purifying step comprises lysing the cells to produce a lysate and subjecting the lysate to immunoadsorption using an immunoreagent that specifically recognizes a viral protein contained within the virus-like particles. In one embodiment, the method further comprises the step of generating an immune response in a mammal by introducing an effective amount of purified virus-like particles into the mammal in a pharmaceutically acceptable carrier. In a preferred embodiment, the immunizing step is performed in a mammal selected from the group consisting of a mouse, rat, rabbit, goat, sheep, horse and human. In one embodiment of the method, the cloned cDNA is produced from an enveloped RNA virus that is a member of the Sindbis-like superfamily or a member of the Flavivirus-like superfamily. Preferably, the cloned cDNA is produced from a member of the group consisting of Togaviridae, Bromovirus, Cucumovirus, Tobavirus, Ilarvirus, Tobravirus, Potexvirus, Flaviviridae, and Pestivirus. In one embodiment of the method, the cloning step comprises cloning a cDNA comprising a 5' untranslated region and sequences coding for hepatitis C virus (HCV) core protein, HCV envelope 1 (E1) protein, HCV envelope 2 (E2) protein and p7 protein, such that the cDNA is capable of being expressed in transfected or infected insect cells, and the maintaining step comprises maintaining the transfected or infected insect cells in culture for about 72 hr to 120 hr, to allow expression of the cDNA to produce HCV structural proteins and allow the HCV structural proteins to form intracellular HCV-like particles. The cloned cDNA may also include sequence that codes for a few amino acids of non-structural protein NS2. One embodiment of the invention is HCV-like particles produced according to this method. In one embodiment, the HCV-like particles further comprise a portion of HCV RNA transcript. The HCV-like particles are about 40 nm to about 60 nm in diameter and have a density of about 1.14 $g/cm^3$ to about 1.18 $g/cm^3$. Another embodiment of the invention is a vaccine comprising the HCV-like particles in a pharmaceutically acceptable carrier. One more embodiment is a therapeutic agent comprising HCV-like particles in a pharmaceutically acceptable carrier. Another embodiment is antibodies produced by immunizing an animal with HCV-like particles, and the antibodies can be monoclonal antibodies. Another embodiment of the invention is a diagnostic kit for detecting HCV infection in an individual comprising HCV-like particles and a, means for detecting antibodies that bind to the HCV-particles.

According to a second aspect of the invention, there is provided a recombinant construct comprising a vector comprising an expression system capable of producing proteins in insect cells in vitro and a DNA complementary (cDNA) to hepatitis C virus (HCV) RNA, wherein the cDNA comprises a 5' untranslated region and sequences coding for HCV core protein, HCV envelope 1 (E1) protein, HCV envelope 2 (E2) protein and p7 protein, such that the cDNA is capable of being expressed in insect cells transfected or infected with the recombinant construct. The recombinant construct may also include sequence coding for at least a part of HCV NS2 protein. One embodiment of this aspect of the invention is insect cells transfected or infected with the recombinant construct.

According to a third aspect of the invention, there are provided recombinant HCV proteins comprising HCV core protein, HCV envelope 1 (E1) protein, HCV envelope 2 (E2) protein and p7 protein that assemble into intracellular HCV-like particles in insect cells.

It should be understood that both the foregoing general description and the following detailed description are exemplary and explanatory only and are not restrictive of the invention as claimed. The accompanying figures, which are incorporated in and constitute a part of the specification, illustrate various embodiments of the invention and, together with the description, serve to explain the principles of the invention.

DETAILED DESCRIPTION OF THE PREFERRED EMBODIMENT

Figure 1:
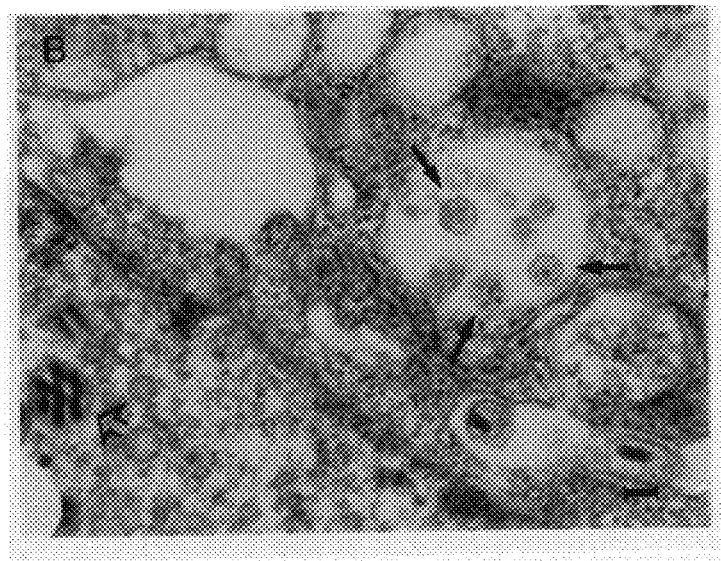
FIG. 1 shows electron microscopy of HCV-like particles (adjacent to solid arrowheads) in large cytoplasmic cisternae of BVHCV-infected insect cells; the bar in the lower right corner represents 50 nm).

Virus-like particles were produced by expressing cDNA coding for structural proteins in a eukaryotic cell expression system. The virus-like particles produced were structurally and biophysically similar to HCV virions, an enveloped RNA virus that infects humans. The virus-like particles comprise at least three viral proteins, a core protein and two envelope proteins, that form a structure having a layered envelope. The particles were produced in the eukaryotic cell cytoplasm, concentrating in cisternae that are presumably derived from the endoplasmic reticulum of the eukaryotic cells. The virus-like particles were purified from the lysed cells. Immunoblot analysis of proteins from the eukaryotic cells in which the virus-like particles were produced showed that high-level viral protein synthesis and appropriate post-translational modification, such as proteolytic cleavage into appropriate sizes and glycosylation, occurred in vitro. Co-immunoprecipitation of viral structural proteins indicated that the virus-like particles assembled intracellularly, which was confirmed by visualization of the intracellular particles by electron microscopy. Biophysical analysis of the partially purified virus-like particles showed that the virus-like particles were similar to virions isolated from humans infected with HCV. These virus-like particles are useful for inducing an immune response, either as a preventive or therapeutic treatment for viral infection. Moreover, the virus-like particles are useful for diagnosing viral infection, particularly for testing human body fluids, to prevent spread of viral disease through infected body fluids. The methods of producing such virus-like particles are useful generally for producing in vitro relatively large quantities of virus-like particles for enveloped RNA viruses, such as members of the Sindbis-like superfamily (Togaviridae, Bromovirus, Cucumovirus, Tobavirus, Ilarvirus, Tobravirus, Potexvirus) and Flavivirus-like superfamily (Flaviviridae, Pestivirus), including, for example, yellow fever virus, dengue viruses, West Nile virus, St. Louis encephalitis virus, Japanese encephalitis virus, Murray Valley encephalitis virus, Rocio virus, tick-borne encephalitis viruses, hepatitis C virus, hepatitis E virus, hepatitis G virus, hog cholera and bovine diarrhea viruses, and border disease virus of sheep.

Hepatitis C virus-like (HCV-like) particles were produced in an insect cell expression system and purified from the lysed cells. A recombinant HCV-baculovirus construct containing HCV cDNA coding for HCV structural proteins was used to express the HCV core protein, the envelope protein 1 (E1), envelope protein 2 (E2), p7 proteins, and a few amino acids of the NS2 protein in insect cells. Typically, using standard methods, the recombinant HCV-baculovirus construct was initially transfected into insect cells and recombinant virus particles produced by the transfected cells were then purified and used to infect additional in vitro cultures of insect cells. Functionally, the transfected and infected cells containing the recombinant HCV-baculovirus construct were substantially identical. Immunofluorescence of recombinant HCV-baculovirus infected insect cells with anti-HCV antibodies and immunoblot analysis of lysates of insect cells infected with the recombinant HCV-baculovirus construct revealed high-level synthesis of HCV structural proteins with appropriate post-translational modification. That is, proteolytic cleavage into appropriate sizes and glycosylation of the E1 and E2 proteins appeared to have occurred in the infected insect cells. The HCV structural proteins assembled intracellularly into HCV-like particles as indicated by co-immunoprecipitation of E2, E1 and core protein from cell lysates. Immunofluorescence analysis of semi-thin section of recombinant HCV-baculovirus infected insect cells with anti-HCV antibodies demonstrated that the expression of HCV structural proteins was confined to the cytoplasm. Cytoplasmic staining showed clusters of immunoreactivity when serum from a HCV-infected individual with high-titre anti-HCV antibodies or specific antibodies against the E1, E2 or core proteins. These anti-HCV antibodies did not display any significant cross-reactivity against insect cell or baculovirus proteins.

Transmission electron microscopy of insect cells infected with the recombinant HCV-baculovirus construct showed abundant virus-like particles of about 40 to 60 nm in diameter, accumulated in cytoplasmic cisternae that are presumably derived from the endoplasmic reticulum of the infected cells. In contrast, no similar particles were found in uninfected insect cells or insect cells infected with a control baculovirus. The virus-like particles were polymorphic in appearance and had an envelope consisting of a membrane. Visualization of the virus-like particles was only possible after osmification, a process that stains membranes. Many of the particles had unevenly distributed electron dense structures within the particles that may be nucleocapsids. The features of these virus-like particles resemble structural and morphological features of pestiviruses in infected cells (Bielefeldt Ohmann, H. & Block, B., *Arch. Virol.* 71:57–74, 1981; Gray E. W. & Nettleton, P. F., *J. Gen. Virol.* 68:2339–2346, 1987; Rice, C. M. "Flaviviridae: the viruses and their replication" in *Fields Virology* (Fields, B. N. et al., eds., Lippincott-Raven Publishers, Philadelphia, Pa.), pp. 931–959, 1996). The virus-like particles formed predominantly into cytoplasmic vesicles, giving the appearance of virion transport through the endoplasmic reticulum (ER) secretory pathway of cells, although no secreted free viral particles were detected in the culture medium. This observation is consistent with the observation that related pestiviruses are not released efficiently from infected cells.

Biophysical characterization of purified HCV-like particles by gradient equbrium centrifugation revealed that the HCV-like particles have a density of about 1.14 g/cm$^3$ to 1.16 g/cm$^3$, similar to the density of virions found in human sera of HCV-infected individuals.

These HCV-like particles apparently result from assembly of HCV structural proteins into virus-like structures that are morphologically and biophysically similar to previously described HCV virions isolated from infected humans. HCV-like particles, purified in large quantities, are useful as a HCV vaccine, HCV therapeutic treatment and for generation of new diagnostic agents for monitoring HCV-infection.

A baculovirus expression system for production of HCV structural proteins in insect cells was used to synthesize HCV-like particles in vitro. The HCV cDNA used was that of the HCV-J strain, genotype 1b, originally cloned from a Japanese patient with chronic hepatitis (Kato N. et al., *Proc. Natl. Acad. Sci. USA* 87: 9524–9528, 1990). The cDNA was subcloned into a helper plasmid (Luckow V. A. et al., *J. Virol.* 67:4566, 1993; pFastBac™ available from GIBCO/BRL, Gaithersburg, Md.). The subcloned cDNA contained 5' untranslated sequences and sequences coding for the core, E1, E2, p7 proteins and few amino acids of the NS2 protein. High-titer recombinant HCV-baculovirus, designated BVHCV, was generated in Sf9 cells. In parallel, a high-titer stock of a control baculovirus construct containing the β-glucuronidase gene, instead of the HCV cDNA, was generated (designated BVGUS). The infection of insect cells with control virus BVGUS served as a negative control.

The monoclonal anti-core, anti E1 and anti E2(G/H) mouse antibodies and the polyclonal anti-E2 rabbit antibody used to detect the HCV structural proteins have been described previously (Dubuisson J. et al., *J. Virol.* 68:6147–6160, 1994; Lesiewski R. et al., *J. Med. Virol.* 45:415–422, 1995). Human sera containing antibodies against HCV were obtained from patients with chronic hepatitis C infections that produce high-titer anti-HCV antibodies. The patients were serological negative for hepatitis B virus, hepatitis A virus and HIV.

The HCV structural proteins were produced in BVHCV-infected insect cells as determined by immunofluorescent analysis, compared to the same type of cells infected with the control baculovirus construct (BVGUS). Insect cells were infected with either the control baculovirus (BVGUS) or the recombinant HCV-baculovirus (BVHCV) and at 72 hr to 120 hr postinfection, usually 96 hr postinfection, the cells were fixed and semi-thin section (0.5 to 1 μm) were produced using standard microscopy procedures. The semi-thin sections were incubated separately with anti-HCV antibodies present in polyclonal rabbit anti-E2 protein antiserum and patient serum. Fluorescein-conjugated anti-IgG antibody was used to reveal the binding of anti-HCV and anti-E2 antibodies when examined using standard fluorescent microscopy. The recombinant HCV-baculovirus directed high-level production of HCV structural proteins as demonstrated by immunofluorescence of infected insect cells using both types of anti-HCV antibodies. The punctate immunostaining patterns of the cytoplasm and cell membrane suggested that the HCV proteins were present in particles or clusters.

The recombinant HCV-baculovirus (BVHCV) also directed a high-level production of HCV structural proteins as demonstrated by immunoblotting of proteins obtained from infected insect cells with antibodies against the HCV structural proteins. To demonstrate this, Sf9 insect cells were infected with either the control baculovirus (BVGUS) or the recombinant HCV-baculovirus (BVHCV) and proteins in cell lysates were analyzed after 72 hr of infection.

The insect cells infected with the negative control baculovirus generally did not produce proteins that were bound by the antibodies directed specifically against HCV proteins.

In the immunoblots corresponding to recombinant HCV-baculovirus infected cell proteins, proteins were recognized by the monoclonal antibodies directed against the HCV core, E1 and E2 proteins. Immunoblotting with the anti-E2 antibody, however, resulted in significant non-specific binding to proteins isolated from insect cells infected with the negative control and the cells infected with the recombinant HCV-baculovirus. Immunoprecipitation with anti-E2 antibodies before immunoblotting removed most of the proteins that were non-specifically bound, showing clearly that E2 protein was produced in the cell infected with the recombinant HCV-baculovirus but not in cells infected with the negative control baculovirus.

Analysis of cell lysates by SDS-PAGE and immunoblotting with monoclonal antibodies against the core, E1 and E2 proteins revealed appropriate post-translational processing of the HCV structural proteins in the insect cells. That is, the core protein had an apparent MW of 21–22 kD, the E1 protein was present in various glycosylated forms with an apparent MW of 30 kD to 35 kD and the E2 protein exhibited an apparent MW of approximately 66 kD. The sizes of these proteins are consistent with post-translational processing of HCV structural proteins in the insect cells because similar sizes have previously been reported for HCV proteins expressed in a mammalian tissue culture system (Miyamura, T. & Matsuura, Y., *Trends Microbiol.* 1(6):229–231, 1993).

Based on the results obtained when proteins produced in insect cells infected with the recombinant HCV-baculovirus were immunoprecipitated with anti-E2 antibodies and then immunoblotted with anti-core or anti-E1 antibodies, the co-immunoprecipitated core, E1 and E2 proteins appear to form a complex in the insect cells. The interaction of the E2, E1 and core proteins was also detected by radioactive metabolic labeling of the recombinant HCV-baculovirus infected insect cells followed by co-immunoprecipitation with anti-E2 antibody using standard procedures. Insect cells infected with the recombinant HCV-baculovirus were labeled with [$^{35}$S]-methionine in vitro and then the cells were collected and lysed substantially as described above. Similarly, insect cells infected with the negative control baculovirus were metabolically labeled and lysed. The cell lysates were immunoprecipitated using anti-E2 polyclonal rabbit antibodies (Lesniewski R. et al., *J. Med. Virol.* 45:415–422, 1995) and the immunoprecipitated radiolabeled proteins were separated by SDS-PAGE substantially as described above. Autoradiography of the gel, using standard methods, revealed that the core, E1 and E2 proteins were co-immunoprecipitated as suggested by the immunoprecipitation and immunoblotting results discussed above.

Although interaction of core and E1 proteins have previously been demonstrated (Lo S.-Y. et al., *J. Virol.* 70(8):5177–5182, 1996) this is apparently the first demonstration of core, E1 and E2 proteins in a co-immunoprecipitable complex produced when just these three HCV proteins are expressed in vitro.

Transmission electron microscopy of BVHCV-infected cells was used to examine the form of these particles containing HCV proteins. For electron microscopy, insect cells in monolayer culture were infected with BVHCV at a multiplicity of infection (MOI) of 10, fixed four days after infection and processed for electron microscopy substantially as described in Example 5 below.

Optimal processing of the infected cells for electron microscopy was crucial for visualization of the HCV-like particles. Preservation of cellular and viral structures with an optimal fixation buffer and a short period of postfixation osmification were important parameters for optimal visualization of the virus-like particles.

Abundant HCV-like particles were seen in cytoplasmic cisternae, presumably derived from the endoplasmic reticulum of the insect cells, as shown in FIG. 1. These particles measured about 40 nm to 60 nm in diameter, had a core, and were surrounded by an envelope consisting of a lipid bilayer membrane. The multiple enveloped, virus-like particles were present in large cellular cisternae that are probably derived from the endoplasmic reticulum. Budding of the particles predominantly occurred into the cytoplasmic cisternae.

In addition to the virus-like particles, polymorphic particles with an apparent diameter of about 20 nm to 100 nm were clustered in large vesicles in the cytoplasm. These polymorphic particles also contained membranous envelopes, but most demonstrated no core-like structures, and may represent partially assembled HCV-like particles or by-products of the expressed HCV structural proteins. Neither HCV-like particles nor polymorphic particles were seen in BVGUS-infected or non-infected insect cells, indicating that the identified structures were related to expression of HCV structural proteins from the recombinant HCV-baculovirus and were not the result of the presence of the baculovirus components of the recombinant vectors.

Figure 2:
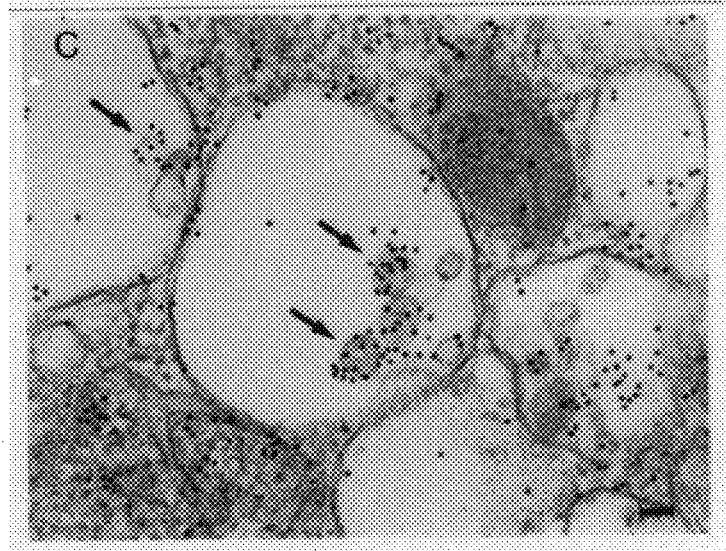
FIG. 2 shows immunogold labeling of the HCV-like particles with anti-E2 antibody as shown by the dark dots near the solid arrowheads; the bar in the lower right corner represents 40 nm.

Immunostaining of these infected cells with anti-HCV human antibodies and anti-E2 antibodies revealed that both the virus-like particles and the vesicular particles structures contained HCV structural proteins. In addition to strong immunostaining of these structures, labeling of the ER was seen with the antibodies, whereas no nuclear staining was observed. As shown in FIG. 2, the HCV-like particles were immunolabeled with anti-E2 antibody and immunogold as shown by the dark dots on and near the HCV-like particles adjacent to the solid arrowheads. Similar results were obtained when the cell sections were immunolabeled with anti-HCV antibodies and immunogold in human serum. That is, the electron dense gold particles that indicate antibody binding were concentrated on the HCV-like particles in the cisternae. The immunolabeling was highly specific for the HCV-like and polymorphic particles. No labeling of any cellular or baculovirus structures were seen in BVGUS-infected or non-infected insect cells. Similarly, no immunofluorescence was seen if samples were not incubated with primary anti-HCV or anti-E2 antibody.

The morphology of these HCV-like particles is consistent with previous ultrastructural characterization of HCV (Feinstone, S. M. et al, *Infect. Immun.* 41:816–821, 1983). That is, the HCV-like particles have morphology similar to HCV detected in cytoplasmic vesicles of a HCV-infected chimpanzee liver, a HCV-infected human B-cell line and HCV-cDNA transfected HeLa cells (Shimizu Y. K. et al., *Hepatol* 23(2):205–209, 1996; Mizuno M. et al., *Gastroenterol.* 109(6):1933–1940, 1995).

The HCV-like particles were purified from lysates of cells infected with the recombinant HCV-baculovirus by CsCl gradient centrifugation to equilibrium, although it will be understood that other forms of centrifugation (e.g., non-equilibrium centrifugation using a step gradient) can equally be used to isolate the virus-like particles. The lysates of cells infected with the recombinant HCV-baculovirus were centrifuged on sucrose or CsCl gradients, and in both types of gradients the HCV-like particles banded in specific fractions confirming assembly of virus-like particles. After purification, the gradient fractions were immunoblotted and the core, E1 and E2 proteins were independently detected in substantially the same gradient fractions, although core immunoreactivity was more widely distributed in the gradients. The density of these HCV-immunoreactive fractions (1.14 to 1.18 g/cm$^3$ in sucrose equilibrium gradients and 1.14 to 1.16 g/cm$^3$ in CsCl equilibrium gradients), was substantially the same density reported for HCV virions visualized by electron microscopy (1.14 g/cm$^3$ to 1.16 g/cm$^3$ as reported by Kaito M. et al., *J. Gen. Virol.* 75:1755–1760, 1994) and or demonstrated by reverse–transcription and polymerase chain reaction (PCR) amplification of HCV genomes (1.03 to 1.20 g/cm$^3$, as reported by Thomssen R. et al., *Med. Microbiol. Immunol.* 181:292–300, 1992; or 1.08 g/cm$^3$, as reported by Miyamoto H. et al., *J. Gen. Virol.* 73:715–718, 1992; or 1.10 to 1.16 g/cm$^3$, as reported by Shindo M. et al., *Proc. Natl. Acad. Sci. USA* 91:8719–8723, 1994).

It will be understood by those skilled in the art that the particles may be purified to substantial purity by other standard techniques such as selective precipitation with substances such as ammonium sulfate, column chromatography, immunopurification and others (see, for example, procedures described by R. Scopes in *Protein Purification: Principles and Practice*, Springer-Verlag, New York, 1982; and "Guide to Protein Purification", *Meth. Enzymol* 182:619–626, 1990).

To further characterize the HCV-like particles, insect cells infected with the recombinant HCV-baculovirus were subjected to sucrose sedimentation velocity centrifugation and gradient fractions were then immunoblotted to reveal co-localization of the HCV structural proteins in high-sedimentation fractions, confirming the presence of virus-like particles. The sucrose gradient fractions were also examined with transmission electron microscopy which revealed structures similar to those seen in insect cells infected with the recombinant HCV-baculovirus.

Figure 3:
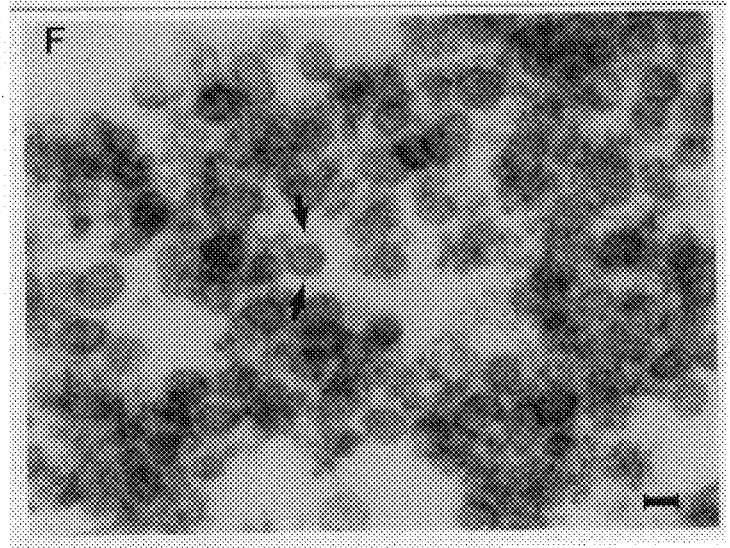
FIG. 3 shows HCV-like particles after purification by sucrose gradient centrifugation; a single particle is adjacent to the solid arrows and the bar in the lower right corner represents 50 nm.

The purified HCV-like particles were examined with transmission electron microscopy as shown in FIG. 3. Similar to the structures seen in BVHCV-infected insect cells (see FIG. 1), the purified HCV-like particles were enveloped virus-like particles of about 40 to 60 nm in diameter. The material shown in FIG. 3 indicates that substantial purification of the HCV-like particles can be readily obtained by gradient centrifugation of cell lysates from recombinant HCV-baculovirus infected insect cells grown in vitro.

Because the HCV-like particles sedimented in density typical of particles containing nucleic acid, the nucleic acid content of the particles was also characterized. The HCV cDNA of the recombinant construct only contained a partial genome expressing the structural proteins and thus may not have contained sufficient information for specific incorporation of nucleic acid into the virus-like particles. To analyze whether the virus-like particles contained nucleic acids, HCV-like particles were purified by immunoprecipitation with anti-E2 antibody. After extensive digestion of non-encepsidated nucleic acids with staphylococcus nuclease and RNase A, the immunoprecipitated viral particles were subjected to nucleic acid extraction using standard methods and the extracted RNA was analyzed by Northern blot analysis, also using standard methods. Nuclease-resistant RNA was hybridized with an HCV-specific probe, showing that the HCV-like particles contained HCV-specific nucleic acid. Treatment of the purified nucleic acids with RNase eliminated all detectable hybridization whereas DNase treatment had no effect, indicating that the particles contained HCV RNA. Identical purification and detection of HCV RNA was obtained when the HCV-like particles were purified by sucrose gradient sedimentation followed by immunoprecipitation.

The HCV RNA incorporated into the HCV-like particles appeared to be somewhat degraded as evidenced by a smear of RNA species in the low molecular weight range. The encapsidated RNA was, however, preferentially encapsidated rather than the result of random incorporation of nucleic acid into the virus-like particles. This was demonstrated by co-infecting the insect cells with the BVHCV recombinant construct and the control construct, BVGUS containing the β-glucuronidase (GUS) coding sequence, or another control construct, BVHIV, containing the coding sequence for HIV gp160. Purification of virus-like particles from the co-infected cells and RNA analysis of the isolated RNA showed the absence of RNA derived from the GUS or HIV gp160 cDNA. Thus, the HCV-like particles preferentially incorporated the HCV transcripts. Although not wishing to be bound to a particular theory or mechanism, the preferential incorporation of HCV transcripts suggests that the HCV transcripts may contain sufficient cis-acting information to interact specifically with the viral structural proteins for encapsidation.

The HCV structural proteins expressed in recombinant HCV-baculovirus infected insect cells appear to undergo appropriate post-translational modification and assemble into a HCV-like particles having a core surrounded by a lipid bilayer envelope. The envelope, presumably containing properly assembled E1 and E2, was labeled specifically by HCV-infected human serum containing high titer of anti-HCV and by anti-E2 antibodies that bind HCV virions. These HCV-like particles have similar morphologic, serologic and biophysical properties as virions isolated from HCV-infected humans.

To the best of the inventors' knowledge, this is the first demonstration that virus-like particles of an enveloped RNA virus can be generated without the other viral components required for viral replication. Previous reports of expression of HCV structural proteins in a baculovirus-insect cell system failed to report HCV-like particle assembly (Matsuura Y. et al., *J. Virol.* 66:1425–1431, 1992; Lanford R. E. et al., *Virol.* 197:225–235, 1993; Matsuura Y. et al., *Virol.* 205:141–150, 1994; Hsu H. H. et al., *Hepatol.* 17(5):763–771, 1993). The recombinant HCV-baculovirus system of the present invention uses an expression construct that contains part of the 5' UTR and the complete structural region including p7 of the HCV-cDNA. Moreover, the time point of insect cell analysis was about 72 hr to 120 hr postinfection whereas earlier reports of HCV protein production generally analyzed the proteins at 24 hr to 48 hr post infection.

Synthesis of HCV-like particles in large quantities is useful for production of a noninfectious HCV vaccine and for reagents for improved diagnostics for HCV infection, particularly to screening blood from donors to prevent post-transfusion acquired HCV. For vaccine production, the HCV-like particles are particularly useful for overcoming some of the problems encountered with vaccines that rely on expression of part of individual structural proteins in soluble form. These soluble single proteins or peptides have met with only marginal success, most likely because the expressed viral proteins are in nonnative forms and lack structural epitopes found on the viral particles and the HCV-like particles of the present invention. In contrast, by using HCV-like particles as an immunogen, a repertoire of neutralizing antibodies can be produced in the vaccinated individual.

Diagnostic Assays

Diagnosis of HCV infection depends on specifically detecting the virus, HCV proteins or anti-HCV antibodies using well known specific binding assays based on immunological techniques (Johnstone et al., *Immunochemistry in Practice,* Blackstone Sci. Pub., Boston, 1987). For example, labeled monoclonal antibodies to HCV structural proteins may be used to detect viral particles or viral proteins in a biological sample. Alternatively, labeled HCV-like particles or proteins purified from the particles can be used to detect the presence of antibodies to HCV or HCV proteins in a biological sample.

Well-known immunoassay formats in which HCV-like particles can be used to detect anti-HCV antibodies include competitive binding assays, direct and indirect sandwich-type immunoassays and agglutination assays (such as described in U.S. Pat. No. 4,956,302 and European Patent No. 0323605). Because the HCV-like particles are structurally related to hepatitis C virions, the HCV-like particles can be used to capture anti-HCV antibodies and antibodies that recognize the HCV-like particles can also recognize HCV. Generally, diagnostic kits using immunoassay formats use the HCV-like particles to assay for anti-HCV antibodies in a human infected with HCV, or use antibodies that bind to HCV-like particles to detect HCV in human tissue (such as blood or serum) obtained from an HCV-infected individual. The detection can be direct or indirect as is well known in the art.

Cell-free assays can be used to measure the binding of human antibodies in serum to HCV-like particles. For example, the particles can be attached to a solid support such as a plate or sheet-like material and binding of anti-HCV antibodies to the immobilized HCV-like particles can be detected by using a labeled anti-human immunoglobulin to visualize the bound anti-HCV antibodies attached to the HCV-like particles on the support (e.g., as the assay described in U.S. Pat. No. 4,861,711). Similarly, HCV-like particles can be attached to inert particles such as latex beads which can be used to detect human anti-HCV antibodies by detecting agglutination or capture of the particles at a discrete position (e.g., assays as described in U.S. Pat. Nos. 5,096,837 and 5,521,102).

HCV-like particles may be labeled using radioactive and nonradioactive labels. The label may be directly or indirectly coupled to the HCV-like particles using methods well known in the art. For example, HCV-like particles may be radioactively labeled with $^3H$, $^{125}I$, $^{35}S$, $^{14}C$ or $^{32}P$ using standard in vivo or in vitro labeling methods and the binding of HCV-like particles to cells, antibodies or compounds found in biological specimens may be detected using autoradiography. Non-radioactive labels appropriate for detecting HCV-like particles include labeled antibodies, fluorophores, chemiluminescent agents, enzymes, colloidal gold or other metals that can bind directly to HCV-like particles or to ligands such as cellular receptor proteins or antibodies that bind to the HCV-like particles.

Prevention and Treatment of HCV Using HCV-like Particles

HCV-like particles are useful for developing new methods of preventing or treating HCV infection. The HCV-particles can be used to assay for proteins, antibodies or other compounds capable of inhibiting interaction between HCV and mammalian cells. For example, compounds that interfere with the ability of HCV to effectively contact human cells can be detected by measuring the ability of labeled HCV-like particles to bind to human cells, in vivo or in vitro, in the presence of the compound compared to control conditions where the compound is not present. Exemplary cell lines for detecting such interference with HCV-like particles include Capan-1, Hep 3B, Hep G2, SK-HEP-1, Chang liver, Daudi, MOLT-4 and WRL 68, all available from the American Type Culture Collection (Rockville, Md.), and HuH7 cells, available from many research laboratories. Similarly, antibodies that interfere with HCV infection of human cells can be detected and their ability to block infection can be measured by assaying the level of interaction between HCV-like particles and human cells (such as hepatocytes and Chang liver or WRL 68 cells) in the presence of the antibodies compared to the level of interaction achieved when the antibodies are absent.

Production of Antibodies that Bind to HCV-like Particles for Diagnostic Detection of HCV Because HCV-like particles appear to mimic hepatitis C virions, antibodies produced specifically against HCV-like particles are useful for binding to HCV or producing a protective immune response in humans (discussed in more detail below). Anti-HCV-like particle antibodies useful for diagnostic kits to detect HCV in human tissues can be readily produced in animals such as a mouse, rat, rabbit, goat, sheep or horse using well known techniques. It will be understood that human antibodies that bind to HCV-particles can be similarly raised by immunizing a human patient or volunteer. Partially purified HCV-like particles are used to immunize the animal generally using a procedure where about 10 to 100 $\mu$g, preferably about 50 $\mu$g, of the particles are initially administered to the animal to induce a primary immune response followed by one to about five booster injections of about 10 to 100 $\mu$g of HCV-like particles over a period of about two weeks to twelve months. Depending on the size of the animal to which the HCV-like particles are administered, the dosage may vary, as will be readily determined by those skilled in the art. The timing and dosage of the booster injections in particular are determined based on the immune response detected in the animal, using methods well known to those skilled in the art. The HCV-like particles are preferably administered subcutaneously as a suspension that includes an adjuvant such as Freund's complete or incomplete adjuvant, although a wide variety of available adjuvants are also suitable. Polyclonal antibodies induced after the primary response to HCV-particles are generally IgM whereas those produced following booster injections are generally IgG, generally reaching levels of 1 to 10 mg/ml of serum. Monoclonal antibodies that bind to HCV-particles can readily be produced by fusing lymphatic cells isolated from an immunized animal using well known techniques as previously described (Milstein & Kohler, *Nature* 256:495–497, 1975; *Nature* 276:269–270, 1978). Polyclonal or monoclonal antibodies that bind to HCV-particles may be bound to a variety of solid supports such as polysaccharide polymers (see U.S. Pat. No. 3,645,852), filter paper, nitrocellulose membranes or beads made of polyethylene, polystyrene, polypropylene or other suitable plastics.

Pharmaceutical Compositions Containing HCV-like Particles for Induction of an Immune Response Vaccination against and treatment of HCV infection may be accomplished using pharmaceutical compositions including HCV-like particles. Suitable formulations for delivery of HCV-like particles are found in *Remington's Pharmaceutical Sciences,* 17th ed. (Mack Publishing Co., Philadelphia, Pa., 1985). These pharmaceutical compositions are suitable for use in a variety of drug delivery systems (Langer, *Science* 249:1527–1533, 1990).

HCV-like particles in compositions are suitable for single administration or in a series of inoculations (e.g., an initial immunization followed by subsequent inoculations to boost the anti-HCV immune response). The pharmaceutical compositions are intended for parenteral, topical or oral administration. Parenteral administration is preferably by intravenous, subcutaneous, intradermal, intraperitoneal or intramuscular administration. Parenteral administration may be preferentially directed to the patient's liver such as by catheterization to hepatic arteries or into a bile duct. For parenteral administration, the compositions can include HCV-like particles suspended in a suitable sterile carrier such as water, aqueous buffer, 0.4% saline solution, 0.3% glycine, hyaluronic acid or emulsions of nontoxic nonionic surfactants as is well known in the art. The compositions may further include substances to approximate physiological conditions such a buffering agents and wetting agents such as NaCl, KCl, $CaCl_2$, sodium acetate and sodium lactate. Aqueous suspensions of HCV-particles can be lyophilized for storage and can be suitably recombined with sterile water before administration.

Solid compositions including HCV-like particles in conventional nontoxic solid carriers such as, for example, glucose, sucrose mannitol, sorbitol, lactose, starch, magnesium stearate, cellulose or cellulose derivatives, sodium carbonate and magnesium carbonate. For oral administration of solid compositions, the HCV-like particles preferably comprise 10% to 95%, and more preferably 25% to 75% of the composition.

HCV-like particles can also be administered in an aerosol such as for pulmonary and/or intranasal delivery. The HCV-like particles are preferably formulated with a nontoxic surfactant (e.g., esters or partial esters of C6 to C22 fatty acids or natural glycerides) and a propellant. Additional carriers such as lecithin may be included to facilitate intranasal delivery.

HCV-like particles can be used prophylactically as a vaccine to prevent HCV infection. Because the HCV-like particles contain only partial HCV genetic information but are like virions in structure, the HCV-like particles are preferred to individual HCV proteins as an immunogenic agent. A vaccine containing HCV-like particles contains an immunogenically effective amount of the particles in a pharmaceutically acceptable carrier such as those described above. The vaccine may further include carriers known in the art such as, for example, thyroglobulin, albumin, tetanus toxoid, polyamino acids such as polymers of D-lysine and D-glutamate, inactivated influenza virus and hepatitis B recombinant protein(s). The vaccine may also include any well known adjuvant such as incomplete Freund's adjuvant, alum, aluminum phosphate and aluminum hydroxide. The immune response generated to the HCV-like particles may include generation of anti-HCV antibodies and/or generation of a cellular immune response (e.g., activation of cytotoxic T lymphocytes or CTL) against cell that present peptides derived from HCV (see Paul, *Fundamental Immunology,* 2nd ed. (Raven Press, New York, N.Y.), for a description of well known immune response mechanisms).

Vaccine compositions containing HCV-like particles are administered to a patient to elicit protective immune response against HCV, which is defined as an immune response that prevents infection or inhibits the spread of infection from cell to cell after an initial exposure to the virus. An amount of HCV-like particles sufficient to elicit a protective immune response is defined as an immunogenically effective dose. An immunogenically effective dose will vary depending on the composition of the vaccine (e.g., containing adjuvant or not), the manner of administration, the weight and general health of the patient and the judgment of the prescribing health care provider. For initial vaccination, the general range of HCV-like particles in the administered vaccine is about 100 $\mu$g to about 1 gm per 70 kg patient; subsequent inoculations to boost the immune response include HCV-like particles in the range of 100 $\mu$g to about 1 gm per 70 kg patient. A single or multiple boosting immunizations are administered over a period of about two weeks to about six months from the initial vaccination. The prescribing health care provider may determine the number and timing of booster immunizations based on well known immunization protocols and the individual patient's response to the immunizations (e.g., as monitored by assaying for anti-HCV antibodies or to avoid hyperimmune responses).

For treatment of a patient infected with HCV, the amount of HCV-like particles to be delivered will vary with the method of delivery, the number of administrations and the state of the person receiving the composition (e.g., age, weight, severity of HCV infection, active or chronic status of HCV infection and general state of health). Before therapeutic administration, the patient will already have been diagnosed as HCV-infected and may or may not be symptomatic. A therapeutically effective dose of HCV-like particles is defined as the amount of HCV-like particles needed to inhibit spread of HCV (e.g., to limit a chronic infection) and thus partially cure or arrest symptoms or prevent further deterioration of liver tissue. Generally, a therapeutically effective dose of HCV-like particles will be in the range of about 1 mg to about 10 gm per day, preferably about 50 mg to about 5 gm per day, and most preferably about 100 mg to 1 gm per day for a 70 kg patient.

Unless defined otherwise, all scientific and technical terms used herein have the same meaning as commonly understood by those skilled in the relevant art. Unless mentioned otherwise, the techniques employed or contemplated herein are standard methodologies well known to one of ordinary skill in the art. The general principles of the present invention may be more fully appreciated by reference to the following non-limiting examples.

EXAMPLE 1

Synthesis of HCV Structural Proteins and HCV-like Particles in Vitro

For the construction of the recombinant HCV-baculovirus, a previously described baculovirus expression system (Luckow V. A. et al., *J. Virol.* 67:4566, 1993) was used (commercially available as BAC-TO-BAC™ from GIBCO/BRL, Gaithersburg, Md.). It will be understood that other baculovirus expression systems could equally be used with minor modifications to the subcloning techniques (e.g., as described in Gheysen D. et al., *Cell* 59:103–112, 1989; Hsu H. H. et al., *Hepatol.* 17(5):763–771, 1993; Zeng C. O.-Y. et al., *J. Virol.* 70:2736–2742, 1996) so long as the HCV cDNA portions (generally, the 5' UTR and the complete structural region including sequence coding for p7 protein) are cloned downstream from an appropriate expression signal in the vector. Other known expression systems for production of the HCV proteins that make up the HCV-like particles (e.g., *Science* 222:524–527, 1983; *Proc. Natl. Acad. Sci. USA* 81:659–663, 1984; *Nature* 296:39–42, 1982) are also well within the scope of those skilled in the art and are considered equivalents of the baculovirus expression system used.

The helper plasmid pFastBacHCVst was generated by subcloning a DNA fragment bounded by EcoRI and Tth111I restriction endonuclease sites, including nt 259 to 2819 of pCMV980 (previously described in detail in Hijikata M. et al., *Proc. Natl. Acad. Sci. USA* 88:5547–5551, 1991). The pCMV980 plasmid contains an 81 nt 5' noncoding region and a 2560 nt coding region of HCV cDNA as deposited previously in the GenBank data base (accession nos. D90208 and D00757). The EcoRI/Tth111I fragment containing HCV cDNA was subcloned into the EcoRI and SpeI restriction endonuclease sites of the pFastbac plasmid. The Tth111I and SpeI restriction endonuclease sites were made blunt-ended with Klenow fragment before ligation. An in-frame translation stop codon is present in the vector sequence close to the 3' end of the subcloned cDNA. The correct sequence of the subcloned fragment in plasmid pFastBacHCVst was confirmed by DNA sequencing and analysis of restriction fragment sizes after digestion with various restriction enzymes. After transposition of the respective sequences into plasmid pBacmid in DH10Bac *E. coli* cells (GIBCO/BRL, Gaithersburg, Md.), the purified recombinant baculovirus DNA was purified using a well known alkaline lysis method. The purified recombinant baculovirus DNA (pBacmidHCVst) was transfected using a standard liposome-mediated gene transfer method (commercially available as CellFectin™ Reagent, GIBCO/BRL, Gaithersburg, Md.) into *Spodoptera frugiperda* Sf9 insect cells that were grown in monolayer culture. The Sf9 insect cells were maintained at 28° C. in serum-free Sf-900 II serum free medium (GIBCO/BRL, Gaithersburg, Md.). It will be understood that the recombinant baculovirus produced in the transfected cells subsequently can infect other insect cells, and that transfected and infected cells are substantially identical. At one to five days after transfection, and generally at three to four days after transfection, the cells were harvested for protein analysis (e.g., by immunofluorescence, immunoblotting or electron microscopy).

The culture medium containing the recombinant HCV-baculovirus (BVHCV) was harvested at the same time. The viral titer of the medium was determined using a routine plaque assay. The virus was amplified by subsequent rounds of infection of Sf9 cells until a final titer of $2 \times 10^9$ pfu/ml was achieved (BVHCV). The high titre BVHCV preparation was used in subsequent infections for analysis of the morphologic and biophysical characteristics of the HCV-like particles. It will be understood that additional high titre preparations of the recombinant HCV-baculovirus (BVHCV) can readily be generated using standard procedures.

For HCV protein expression, the Sf9 cells were infected with an MOI of 10, during mid-log growth (either in spinner or monolayer culture), although infection at an MOI of between 1 and 100 is also appropriate.

In a parallel construction, a control baculovirus (BVGUS) was generated by subcloning the coding sequence of the enzyme β-glucuronidase (GUS) into the same vector in position for expression, producing a final titre stock of $2 \times 10^9$ pfu/ml. Infection of Sf9 cells with the BVGUS baculovirus at MOI of 10 under conditions substantially identical to those used for infection with the BVHCV construct served as negative control, although infection at an MOI of 1 to 100 would also be appropriate.

Detection of HCV protein expression, synthesis of HCV-like particles and polymorphic particles and partial purification of the HCV-like particles is described in detail in the Examples that follow.

EXAMPLE 2

Immunofluorescent Analysis of HCV Proteins Produced in Insect Cells

Insect cells were independently infected with the negative control baculovirus (BVGUS) and the recombinant HCV-baculovirus (BVHCV) at an MOI of 10 and grown in vitro substantially as described above. At 96 hr postinfection, the cells were fixed and semi-thin sections were produced using standard microscopy procedures for both types of infected cells. The semi-thin sections were incubated separately with anti-HCV antibodies present in polyclonal rabbit anti-E2 protein antiserum and patient serum (diluted 1:200 in a 1% solution of bovine serum albumin in phosphate buffered saline solution (1% BSA/PBS) and then with a fluorescein-conjugated anti-IgS antibody (diluted 1:500; from Jackson Laboratories). Between steps, plates were rinsed three times with PBS. The immunofluorescence was detected by microscopy when the sections were exposed to 520 nm.

EXAMPLE 3

Immunoblotting Analysis of HCV Proteins Produced in Vitro

High-level production of HCV structural proteins from the recombinant HCV-baculovirus (BVHCV) was demonstrated by immunoblotting proteins obtained from infected insect cells with antibodies against HCV structural proteins. Sf9 insect cells were infected with either the control baculovirus (BVGUS) or the recombinant HCV-baculovirus (BVHCV) as described above and at 72 hr postinfection, the cells were lysed with lysis buffer containing 0.5% Nonidet P-40 (NP-40), 50 mM Tris, 50 mM NaCl, 5 mM EDTA, pH 7.5 and 0.5 mM phenylmethylsulfonyl fluoride (PMSF). The cell lysates were cleared of cell debris and nuclei by low-speed centrifugation ($10,000 \times g$ at 4° C.). After centrifugation, portions of the lysates containing about 50 µg of protein were separated by SDS-polyacrylamide gel electrophoresis (SDS-PAGE) on 12% gels under conditions that allowed separation of proteins having an apparent molecular weight (MW) ranging from 7 kD to 100 kD as determined from the separation of molecular weight markers separated simultaneously in the gel. Other portions of the lysates containing about 50 µg of protein were immunoprecipitated with anti-E2(9284) antibody (a polyclonal rabbit antibody as described in Lesniewski R. et al., *J. Med. Virol.* 45:415–422, 1995) using standard immunoprecipitation methods. The immunoprecipitated proteins were then separated on 12% SDS-PAGE gels in parallel to the total lysate proteins as described above. After gel separation, the proteins were transferred to PVDF membranes (Schleicher & Schuell) using standard immunoblotting methods and the blots were individually probed with monoclonal antibodies as follows: an anti-core antibody (diluted 1:2000), an anti-E1 antibody (diluted 1:1000) and an anti-E2(G/H) (diluted 1:1000) antibody. After the anti-HCV protein antibodies were allowed to bond to the membrane–bound proteins, horseradish peroxidase-conjugated anti-mouse-IgG antibody (diluted 1:4000; from Amersham) were allowed to bind to the antibodies and binding was visualized by chemiluminescence detection (commercially available as ECL™ Kit, from Amersham).

Immunoblotting with monoclonal antibodies against the core, E1 and E2 proteins revealed appropriate post-translational processing of the HCV structural proteins. The core protein (MW 22 kD), the E1 protein, present in various glycosylated forms (MW 30 kD to 35 kD) and the E2 protein (MW 66 kD) were all individually detected by immunoblotting. Immunoprecipitation was performed using standard methods. Briefly, after washing the infected cell monolayers with PBS, the cells were harvested with NP-40 lysis buffer as described above. Aliquots (400 µl) of the cleared supernatant from the BVHCV-infected and control BVGUS-infected cells were separately incubated with 1 μl of anti-E2(9284) antibody for 16 hours at 4° C. and then mixed with 50 of protein A-sepharose 4B-Cl beads (Pharmacia) for 1 hr at 4° C. The beads were washed repeatedly and the proteins bound to the beads were released and denatured by heating for 5 min at 95° C. in SDS sample buffer (Laemmli U. K., Nature 227:680–685, 1970). The proteins were separated by SDS-PAGE in a 12% polyacrylamide gel before immunoblotting using standard protein transfer and immunodetection procedures.

Anti-core antibodies bound to about seven bands of protein present in the total protein lysate ranging in size from about 20 kD to about 80 kD, with the most prominent band being the 22 kD core protein band. In the proteins fractionated by immunoprecipitation before immunoblotting, a single band of 22 kD protein was the predominant protein detected although faint bands of about 40 kD. Thus, immunoprecipitation with anti-E2 antibody precipitated HCV core protein also, suggesting that core protein and E2 protein expressed in insect cells form part of a protein complex.

Anti-E1 antibodies bound to about three bands of protein present in the total protein lysate ranging in size from about 10 kD to about 35 kD, with 10 kD band representing nonspecific binding because it was also seen in the cell proteins of the negative control lysate without immunoprecipitation. The most prominent bands HCV-specific proteins were a pair of bands of about 30 kD to 35 kD, probably representing different glycosylated forms of the HCV E1 protein. In the proteins fractionated by immunoprecipitation before immunoblotting, there was significantly more of these two 30 kD and 35 kD bands than seen without immunoprecipitation indicating that the immunoprecipitation concentrated the E1 proteins. Thus, immunoprecipitation using anti-E2 antibodies specifically concentrated E1 proteins suggesting that the E1 and E2 proteins expressed in the insect cells are present in a protein complex.

Immunoblotting using anti-E2 antibodies revealed considerable nonspecific binding to about twelve proteins in both the negative control cell lysate and the recombinant HCV-baculovirus infected cell lysate, although a band about 66 kD, the MW of E2 protein, was significantly more predominant in the immunoblot of the recombinant HCV-baculovirus infected cell lysate compared to that of the negative control. In the proteins fractionated by immunoprecipitation before immunoblotting, the nonspecific binding by anti-E2 antibody during immunoblotting was reduced to a single protein of MW about 50 kD, seen in both the negative control lysate and the lysate from cells infected with recombinant HCV-baculovirus, whereas E2 protein of MW 66 kD was only seen in the lysate from cells infected with recombinant HCV-baculovirus.

These results show that immunoprecipitation with anti-E2 antibodies co-precipitates HCV core, E1 and E2 proteins suggesting that all three proteins form a complex in the insect cells.

EXAMPLE 4

Metabolic Labeling and Immunoprecipitation of HCV Structural Proteins Produced in Vitro Subconfluent monolayers of Sf9 insect cells in 10 cm dishes were infected with BVHCV and BVGUS at a MOI of 10 and grown in vitro substantially as described above. At 72 hours after infection, the cells were washed with prewarmed medium lacking methionine and cysteine and incubated with the same medium for an additional 60 min. Then, the infected cells were labeled for 30 min with 250 μCi $^{35}$S-methionine and $^{35}$S-cysteine (DuPont NEN). Immunoprecipitation was performed substantially as described above using 400 μl aliquots of the cleared supernatants from the BVHCV-infected and control BVGUS-infected cells which were separately incubated with 1 μl of anti-E2(9284) antibody (16 hr, 4° C.) and then mixed with 50 μl of protein A-sepharose 4B-Cl beads (Pharmacia) (1 hr, 4° C.). After the beads were washed repeatedly, the bound proteins were released and denatured in SDS sample buffer (5 min, 95° C.) (Laemmli U. K., Nature 227:680–685, 1970) and separated by SDS-PAGE in a 12% gel followed by autoradiography using standard methods.

After immunoprecipitation with anti-E2(G/H) antibodies and protein separation, autoradiography of the gel revealed that the core, E1 and E2 proteins were co-immunoprecipitated. That is, immunoprecipitation with anti-E2 antibodies co-precipitated radiolabeled E2, E1 and core proteins as determined by their respective sizes on the autoradiograph relative to MW standards.

EXAMPLE 5

Electron Microscopy and Immunogold Labeling of HCV-like Particles

For electron microscopy, subconfluent monolayers of Sf9 insect cells were infected with BVHCV and BVGUS and grown in vitro as described above. At four days after infection, the cells were washed with PBS and fixed in various solutions for morphological studies (in 1.25% formaldehyde, 2.5% glutaraldehyde, 0.03% picric acid, 0.05 M cacodylate and 0.03% $CaCl_2$ at pH 7.4 (Buffer A)); for immunogold labeling (in 7% formaldehyde, 0.25 M sucrose, 0.03% picric acid, 0.05M cacodylate and 0.03% $CaCl_2$ at pH 7.4 (Buffer B)). The cells were scraped from the cell culture dishes with a razor blade, pelleted in a microcentrifuge (10 min, 14,000 rpm) and then fixed with 1% osmium tetroxide in 0.05M cacodylate buffer for 15 to 60 min. The pellets were washed in 0.1 M maleate buffer (pH 5.0), treated with 1% uranyl acetate pH 5.0 for 30 min, washed with maleate buffer, dehydrated in a graded series of ethanol solutions and proprylen oxide, and finally embedded in a mixture of Epon 812 and Araldite. Thin sections were stained with fresh uranylacetate in 50% acetone and lead citrate and examined. Prior to immunogold labeling, semi-thin sections were transferred to glass slides and immunofluorescence with patient anti-HCV and anti-E2(9284) was performed as described above. For immunogold labeling, ultrathin sections collected on nickel grids were etched with saturated $NaIO_4$. After washing with PBS, the grids were incubated with 3% BSA in PBS for 30 min. The grids were then incubated for 1 hr with either anti-HCV (HCV patient serum; dilution 1:100 in 1% BSA/PBS), anti-E2 (polyclonal anti-E2 rabbit serum 9284; dilution 1:50 in 1% BSA/PBS) or 1% BSA/PBS only. After five washes with PBS, samples were incubated with protein A coupled to 10 nm gold particles in PBS (dilution 1:200) and rinsed five times with PBS. After counterstaining with uranyl acetate and lead citrate, samples were examined by transmission electron microscopy (using a JEOL 1200 EX microscope at 80 kV).

EXAMPLE 6

Purification of HCV-like Particles

To purify the HCV-like particles, lysates of recombinant baculovirus-infected insect cells were subjected to sucrose

OTHER PUBLICATIONS

Grakoui et al., *Proc. Natl. Acad. Sci. USA*, 90: 10583–10587, 1993, "A second hepatitis C virus–encoded proteinase."

Gray & Nettleton, *J. Gen. Virol.*, 68: 2339–2346, 1987, "The Ultrastructure of Cell Cultures Infected with Border Disease and Bovine Virus Diarrhoea Viruses."

He et al., *J. Infect. Dis.*, 156: 636–640, 1987, "Determining the Size of Non–A, Non–B Hepatitis Virus by Filtration."

Hijikata et al., *Proc. Natl. Acad. Sci. USA*, 88: 5547–5551, 1991, "Gene mapping of the putative structural region of the hepatitis C virus genome by in vitro processing analysis."

Hijikata et al., *J. Virol.*, 67: 1953–1958, 1993, "Equilibrium Centrifugation Studies of Hepatitis C Virus: Evidence for Circulating Immune Complexes."

Hoofnagle & DiBiscecile, *New England Journal of Medicine*, 336: 347–356, 1997, "The Treatment of Chronic Viral Hepatitis."or CsCl gradient centrifugation using standard procedures substantially as described previously (Miyamoto H. et al., *J. Gen. Virol.* 73:715–718, 1992; Hijikata M. et al., *J. Virol.* 67:1953–1958, 1993). Insect cells were infected with recombinant-HCV-baculovirus (BVHCV) at MOI of 10 and the infected cells were cultured as described in Example 1. At four days postinfection, the BVHCV-infected cells were lysed, subjected to low-speed centrifugation substantially as described above. The supernatant was then layered over a 30% sucrose/PBS (w/v) cushion and centrifuged at 150,000×g for 6 hr at 4° C. The pellet under the sucrose cushion was collected and resuspended in 500 μl 1 mM PMSF in PBS and the resuspended material was then centrifuged into a sucrose or CsCl gradient.

For sucrose centrifugation, the pellet was layered onto a 20% to 60% sucrose/PBS (w/v) gradient and centrifuged at 150,000×g for 22 hr at 4° C. Ten 0.5 ml fractions were collected from the top of the gradient and separated by SDS-PAGE on a 12% gel substantially as described above. For CsCl centrifugation, 0.5 ml of the pellet was mixed with 4.5 ml of PBS containing 0.5 mM PMSF and 1.67 g CsCl (33% w/v) and centrifuged at 280,000×g for 72 hr at 4° C. After centrifugation, ten 0.5 ml fractions were collected from the top and extensively dialyzed against PBS at 4° C. and then analyzed by SDS-PAGE on a 12% gel as described above.

After SDS-PAGE separation, the proteins were transferred to a membrane for immunoblotting substantially as described above. The membrane was probed with anti-core, anti-E1, or anti-E2(G/H) antibody and horseradish peroxidase labeled anti-mouse antibody as described above. In both sucrose and CsCl gradients, the HCV-like particles banded in specific density fractions that were generally fractions 6 through 9, with most of the protein found in fractions 6 and 7. The proteins in these fractions were immunolabeled with all three antibodies, confirming assembly of virus-like particles. The density of the fractions containing immunoreactive proteins of the HCV-like particles was 1.14 g/cm$^3$ to 1.18 g/cm$^3$ in sucrose gradients and in 1.14 g/cm$^3$ to 1.16 g/cm$^3$ in CsCl gradients. This density range for HCV-like particles substantially coincided with the density of fractions of sucrose equilibrium centrifugation that contained HCV from human plasma (1.14 g/cm$^3$ to 1.16 g/cm$^3$). Moreover, the density of the HCV-like particles is similar to the density reported previously for HCV genomes (1.03 g/cm$^3$ to 1.20 g/cm$^3$) (Kaito, M. et al., *J. Gen. Virol.* 75:1755–1760, 1994).

For electron microscopy of purified virus-like particles using procedures substantially as described above, sucrose gradient fractions were pooled, diluted 1:10 with PBS and subjected to a second ultracentrifugation (Beckman SW55 rotor, 40,000 rpm for 2 hr at 4°). The pellet was fixed in fixation Buffer A and subjected to the same processing as described above. As shown in FIG. 3, the purified HCV-like particles were similar to the structures seen in BVHCV-infected insect cells (see FIG. 1). The purified enveloped HCV-like particles were about 40 to 60 nm in diameter. These results show that quantities of substantially pure HCV-like particles can be readily obtained from cell lysates from recombinant HCV-baculovirus infected insect cells grown in vitro.

EXAMPLE 7

Production of an Immune Response to HCV-like Particles In Vivo

An immune response against HCV-like particles was produced in vivo by injecting purified HCV-like particles into BALB/c mice. Anti-HCV-specific antibodies were detected by immunofluorescence using sera taken from the immunized mice.

Sf9 insect cells were grown in suspension culture to approximately 1×10$^6$ cells per ml (250 ml total volume, maintained at 28° C. in serum-free medium) and were infected at MOI of 10 with the recombinant HCV-baculovirus construct, BVHCV, substantially as described in Example 1. At 96 hr postinfection, the cells were lysed and HCV-like particles were purified by sucrose gradient centrifugation as described in Example 6. The partially purified particles were analyzed by silver staining using standard protein detection methods and by immunoblotting as described in Example 3 using antibodies against HCV structural proteins. The protein concentration of the partially purified particles was approximately 0.5 mg/ml.

The purified particles were mixed 1:1 (v:v) with Freund's complete adjuvant (Difco Laboratories, Detroit, Mich.) for the initial immunization, and 1:1 (v:v) with Freund's incomplete adjuvant (Difco Laboratories) for the booster immunizations (as described in: Harlow, E. & Lane, D. *Antibodies. A Laboratory manyal*, Cold Spring Harbor Laboratory, Cold Spring Harbor, N.Y. 1988).

Female BALB/c mice (3 to 6 weeks old, from Charles River Laboratories) were immunized by i.p. injection of 200 μl of HCV-like particles in Freund's complete adjuvant. Four to twelve weeks later, the mice were boosted by i.p. injection of 200 μl of HCV-like particles in Freund's incomplete adjuvant. As a control, BALB/c mice were immunized with fractions similarly prepared from BVGUS-infected insect cells. At fourteen weeks after the initial immunization, mouse sera were obtained from the tail veins using conventional methods. Sera from mice immunized with HCV-like particles and control BVGUS fractions were analyzed for the presence of HCV-specific antibodies using an immunofluorescence assay (substantially as described in Example 2) and COS7 cells that had been transfected with the cDNA for the HCV structural proteins (pCDHCVst) to produce intracellular HCV proteins.

Briefly, COS7 cells were transfected with 5 μg of purified pCDHCVst DNA per 10 cm dish (using standard DEAE Dextran transfection methods). On day 3 post-transfection, the cells were fixed in a 50:50 (v:v) mixture of methanol and acetone and incubated with individual mouse serum (dilution 1/100 to 1/200 in PBS containing 1% BSA). After washing away unbound antibody with PBS, the cells were incubated with a FITC-conjugated anti-mouse-IgG antibody (diluted 1/200 in PBS containing 1% BSA; Jackson Laboratories, West Grove, Pa.). The plates were rinsed with PBS several times after the incubation steps and immunofluorescence was detected microscopically, as described in Example 2.

HCV-specific cytoplasmic cell immunofluorescent staining was detected with the sera obtained from mice immunized with the HCV-like particles. The sera from mice immunized with HCV-like particles demonstrated a specific immunoreactivity against the HCV structural proteins expressed in the COS7 cells. In contrast, sera from control mice immunized with BVGUS fractions showed no detectable immunoreactivity against the HCV protein in the pCDHCVst-transfected COS7 cells. Similarly, sera obtained from mice immunized with HCV-like particles showed immunoreactivity with BS-C-1 cells (African Green Monkey kidney cell line available from the ATCC, Rockville, Md.) infected with recombinant vaccinia virus expressing HCV structural proteins (vvHCV). In immunoblats of cell lysates of vvHCV-infected BSC1 cells, the sera from mice immunized with HCV-like particles demonstrated a specific immunoreactivity against the HCV core protein.

These results show that the HCV-like particles are effective at producing an HCV-specific immune response in vivo and are thus useful for producing an anti-HCV vaccine.

Although the present invention has been described in the context of particular examples and preferred embodiments, although it will be understood that the invention includes other legally equivalent embodiments that will be recognized by those skilled in the art.

What is claimed is:

1. A method of producing an isolated non-infectious hepatitis C virus (HCV) virus-like particle (VLP) having structural epitopes found on native infectious HCV particles comprising the steps of:
   (a) constructing recombinant DNA encoding HCV core protein, HCV envelope 1 (E1) protein, and HCV envelope 2 (E2) protein;
   (b) expressing said recombinant DNA in a eukaryotic host cell for sufficient time to allow production of said HCV core protein, HCV E1 protein, and HCV E2 protein and assembly of a non-infectious HCV VLP comprising said HCV core protein, HCV E1 protein, and HCV E2 protein; and
   (c) isolating said non-infectious HCV VLP from said eukaryotic host cell, whereby said isolated non-infectious HCV VLP possesses structural epitopes found on native infectious HCV particles.

2. The method of claim 1, wherein said constructing step further comprises constructing said recombinant DNA further to encode HCV p7 protein, said expressing step further comprises expressing said recombinant DNA further to allow production of said HCV p7 protein and assembly of said non-infectious HCV VLP further comprising said HCV p7 protein, and said isolating step further comprises isolating said non-infectious HCV VLP further comprising said HCV p7 protein.

3. The method of claim 2 wherein said recombinant DNA is cDNA comprising HCV 5' untranslated region (UTR) and sequence encoding said HCV core protein HCV E1 protein, HCV E2 protein, and HCV p7 protein.

4. The method of claim 3 wherein said cDNA further comprises sequence encoding at least a part of HCV NS2 protein.

5. The method of claim 1 wherein said isolating step comprises lysing said eukaryotic host cell to produce a lysate and subjecting said lysate to sucrose or CsCl gradient centrifugation.

6. The method of claim 1 wherein said isolating step comprises lysing said eukaryotic host cell to produce a lysate and subjecting said lysate to immunoadsorption using an immunoreagent that specifically recognizes a viral protein contained within said VLP.

7. The method of claim 1 wherein said expressing step is permitted to proceed about 72 hr to 120 hr.

8. The method of claim 1 wherein said recombinant DNA is a baculovirus vector.

9. The method of claim 1 wherein said eukaryotic host cell is an insect cell.

10. An isolated non-infectious HCV VLP produced by the method of any of claims 1–9.

11. An immunogenic composition comprising an isolated non-infectious HCV VLP produced by the method of any of claims 1–9 in a pharmaceutically acceptable carrier.

* * * * *